United States Patent [19]
Blanchard et al.

[11] Patent Number: 5,707,587
[45] Date of Patent: Jan. 13, 1998

[54] APPARATUS FOR IN SITU, NON-INVASIVE POLYMER CURE DETERMINATION

[75] Inventors: Gary J. Blanchard, Okemos; Julie L. Jessop, Lansing; Alec B. Scranton, East Lansing, all of Mich.

[73] Assignee: Board of Trustees operating Michigan State University, East Lansing, Mich.

[21] Appl. No.: 752,830

[22] Filed: Nov. 20, 1996

Related U.S. Application Data

[62] Division of Ser. No. 427,454, Apr. 24, 1995, Pat. No. 5,633,313.

[51] Int. Cl.$^6$ .................................. G01N 21/64
[52] U.S. Cl. ........................ 422/82.08; 436/172
[58] Field of Search .................. 422/82.06, 82.08, 422/82.05, 82.07; 436/172

[56] References Cited

U.S. PATENT DOCUMENTS

| | | |
|---|---|---|
| 3,551,344 | 12/1970 | Gardlund et al. |
| 3,557,218 | 1/1971 | Hall et al. |
| 3,716,595 | 2/1973 | Hall et al. |
| 3,728,394 | 4/1973 | Hall et al. |
| 4,722,983 | 2/1988 | Monnier . |
| 4,941,997 | 7/1990 | Decher et al. |
| 5,068,318 | 11/1991 | Decher . |
| 5,100,802 | 3/1992 | Mickols ................ 436/34 |
| 5,137,800 | 8/1992 | Neckers et al. |
| 5,158,720 | 10/1992 | Levy . |

FOREIGN PATENT DOCUMENTS 353650  2/1990  Japan.

OTHER PUBLICATIONS

"Process Monitoring Sensors For Polymer Composites", U.S. Department of Comerce, Report #NISTIR 4514 (1991).
Levy, R. L., and S. D. Schwab, Polymer Composites 12 96 (1991).
Wang, F. W., et al., in "Photophysics of Polymers", edited by C.E. Hoyle and J. M. Torkelson, ACS, Washington, D.C. 33 454–462 (1987).
ACS Symposium Series, Chapter 9, 367 (1988).
Stroeks et al (Stroeks, A., et al., Polymer 29 467 (1988).
Scarlata, S.F., et al., Polymer Comm. 27 41 (1986).
Tan, W. et al., Science 258 778–781 (1992).
Holtom, Gary R., ASTM Proceedings, 1204–01 (1990).
Blanchard, G.J., Chemical Physics 138 365–375 (1989).
Blanchard, et al., J. Phys. Chem. 92 5850–5854 (1988).
Karpovich and Blanchard, J. Phys. Chem., 99: (1995).

Primary Examiner—Jeffrey Snay
Attorney, Agent, or Firm—Ian C. McLeod

[57] ABSTRACT

A method and apparatus (10) for detection of the degree of cure of a polymer in situ and non-invasively. The method and apparatus uses a solvatochromic probe molecule which upon curing produces a shift in the fluorescence emission spectrum as compared to a liquid polymerizable composition. The method and apparatus is particularly adapted for poly(vinyl) polymers. Preferred solvatochromic probe molecules are oxazones and pyrene.

4 Claims, 9 Drawing Sheets

APPARATUS FOR IN SITU, NON-INVASIVE POLYMER CURE DETERMINATION

This is a divisional of application(s) Ser. No. 08/427,454 filed on Apr. 24, 1995 now U.S. Pat. No. 5,633,313.

BACKGROUND OF THE INVENTION

(1) Field of the Invention

The present invention relates to a method and apparatus which uses a solvatochromic probe molecule admixed in a polymerizable composition in order to determine when a cured polymer is produced. There is a wavelength or intensity shift in the fluorescence spectrum of the probe molecule in the cured polymer as compared to the uncured polymer. In particular, the present invention relates to a method wherein a ratio of the fluorescence intensity of the probe molecule in the polymerizable composition to the fluorescence intensity of the probe molecule in the cured polymer is determined at different wavelengths related to the shift in fluorescence spectrum produced upon curing.

(2) Description of Related Art

In the field of polymer and composites processing, there is a compelling need for the development of inexpensive on-line sensors for determining viscosity and degree of cure. For example, the manufacture of polymer-matrix composites involves a series of complex chemical and physical changes which must be adequately controlled to produce products with desirable properties. Due to the lack of appropriate on-line sensors for properties such as viscosity and degree of cure, most quality control efforts are based on off-line measurements made after the product has completed its cure cycle. On-line monitoring sensors which could be interfaced with an electronic control scheme would significantly enhance the reliability of polymer and composites processing methods while reducing the cost.

The need for such sensors has been recognized widely, and the measurement of a variety of physical phenomena has been explored, including dielectric constant and loss, acoustic and ultrasonic wave propagation, and optical techniques ("Process Monitoring Sensors for Polymer Composites," U.S. Department of Commerce, Report #NISTIR 4514 (1991)). To date, none of these approaches has resulted in the development of an inexpensive on-line sensor.

Fluorescence techniques have been proposed for the development of on-line viscosity sensors due to the fact that the fluorescence behavior of a variety of molecular probes depends on the local viscosity. For example, many fluorescent probes exhibit an enhanced fluorescence intensity with increasing viscosity due to decreased non-radiative energy transfer. Levy and Schwab (Levy, R. L., and S. D. Schwab, Polymer Composites 12 96 (1991) and U.S. Pat. No. 5,158,720) and Wang et al. (Wang, F. W., et al., in "Photophysics of Polymers", edited by C. E. Hoyle and J. M. Torkelson, ACS, Washington, D.C. (1987)) demonstrated that such an increase in fluorescence intensity can be used to monitor the viscosity increase during cure. Another publication is Chapter 9 of ACS Symposium Series 367 (1988). The measurement of absolute fluorescence intensity, however, has some significant limitations. For example, the method has limited utility for monitoring the degree of cure above the gel point (limited dynamic range) and is subject to uncertainty due to variations in background fluorescence. Stroeks et al. (Stroeks, A., et al., Polymer 29 467 (1988)) investigated the use of viscosity-sensitive excimer formation to monitor degree of cure. In addition to the aforementioned limitations of the previous technique, the investigators concluded that apparent intensity changes in the excimer peak were actually dominated by changes in the intensity of the overlapping monomer peak (which was increasing because of reduced non-radiative transfer). Finally, Scarlata and Ors (Scarlata, S. F., et al., Polymer Comm. 27 41 (1986)) have monitored an increase in fluorescence polarization which they attribute to a viscosity-induced decrease in the rotational mobility of the probe molecule. However, due to its complexity, this technique is unlikely to form the basis for an inexpensive on-line sensor for polymer and composites processing due to its need to measure absolute quantities. See also Tan, W. et al., Science 258, 778–781 (1992); Holtom, Gary R., ASTM Proceedings, 1204-01 (1990); Wang, F. W., ACS, 33 454462 (1987).

Solvatochromic compounds are known to the prior art. Such compounds are described in U.S. Pat. Nos. 4,941,997 to Decher et al.; 5,068,318 to Decher; 4,722,983 to Monnier et al. and EP 353650 to Hayashi et al.

A number of compounds used in photopolymerization of vinyl monomers can also be solvatochromic, such as described in U.S. Pat. No. 5,137,800 to Neckers et al. U.S. Pat. Nos. 3,716,595, 3,557,218 and 3,728,394 to Hall et al. describes photochromatic dihydropyrenes. U.S. Pat. No. 3,551,344 to Gardlund et al. describes photochromatic polyaromatic compounds used in plastics. Some polymers are photoconductive.

Blanchard, G. J., Chemical Physics 138 365–375 (1989); Blanchard et al., J. Phys. Chem. 92: 5850–5854 (1988); and Karpovich and Blanchard, J. Phys. Chem., 99:3951–3958 (1995) describe various dyes which can be solvatochromic.

OBJECTS

It is therefore an object of the present invention to provide a novel method and apparatus for determining the degree of cure of a polymer. In particular it is an object of the present invention to provide a method which is relatively simple and economical. These and other objects will become increasingly apparent by reference to the following description and the drawings.

BRIEF DESCRIPTION OF DRAWINGS

FIG. 2 shows a distinct shift in peak emission wavelength after about 40 minutes.

DESCRIPTION OF PREFERRED EMBODIMENTS

Figure 1:
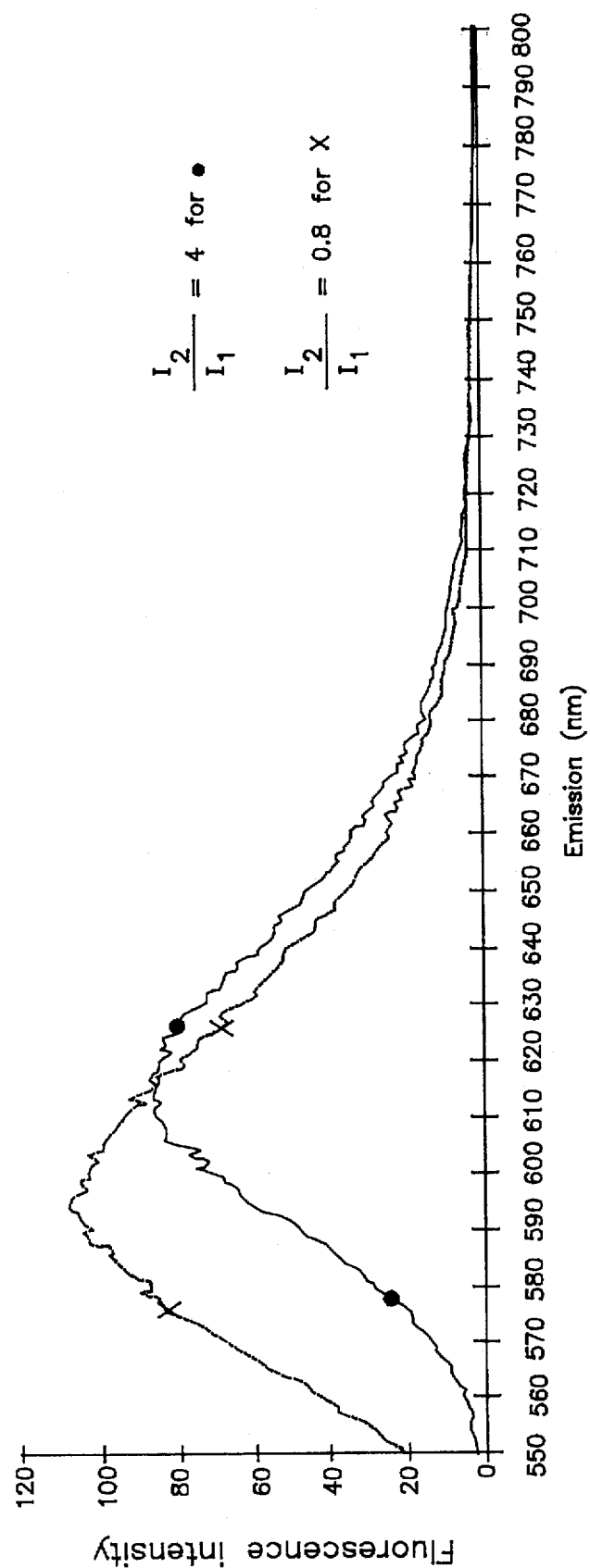
FIG. 1 is a graph of fluorescence intensity versus light emission at the listed wavelengths in nanometers for a vinyl ester and an initiator (AIBN) with $10^{-4}$ weight percent phenoxazone as a probe molecule at 70° C. and at 540 nm excitation ($\lambda_{exc}$) in a composition as set forth in Example 1. The solid line is for the reaction mixture prior to curing and the dotted line is after curing for 60 minutes. A distinct shift in the emission peak upon curing is shown.

The present invention relates to a method for determining a degree of curing of a liquid polymerizable composition to a cured polymer which comprises: providing a solvatochromic probe molecule in a reaction mixture with the liquid polymerizable composition which is curable to the cured polymer, the probe molecule having a first fluorescence emission spectrum in the reaction mixture; and curing the fluid reaction mixture to produce the cured polymer with measurement of the emission fluorescence spectrum, wherein during the curing to produce the polymer the reaction mixture exhibits a shift in the first fluorescence emission spectrum to a second fluorescence emission spectrum because of the probe molecule so that the degree of curing to the cured polymer is determined.

Further, the present invention relates to a method for determining a degree of cure of a polymer which comprises: introducing a solvatochromic probe molecule into a reaction mixture with a liquid polymerizable composition which can be cured into a cured polymer, wherein the probe molecule has a fluorescence emission spectrum which changes during curing; and monitoring the fluorescence emission spectrum of the probe molecule in the reaction mixture during curing, wherein there is a shift in an initial fluorescence emission spectrum of the probe molecule in the reaction mixture to a final fluorescence emission spectrum of the probe molecule in the cured polymer; and comparing a change in the fluorescence emission spectrum to a preceding fluorescence emission spectrum at different times so as to detect the degree of cure.

Finally, the present invention relates to an apparatus for determining an extent of curing of a cured polymer which comprises: a detection means which measures a shift in fluorescence emission spectrum during the curing of a liquid polymerizable composition to the cured polymer from a solvatochromic probe molecule, wherein the probe molecule has a first emission fluorescence spectrum in the liquid polymerizable composition and a shifted second fluorescence emission spectrum in the cured polymer, wherein the detection means includes a probe means mounted adjacent to the polymer for detecting the fluorescence; a light source which can be directed at the polymerizable composition so that the fluorescence emission spectrum produced by the probe molecule is detected by the probe means; a support for the fluid polymer during the curing to the cured polymer; and calculating means for calculating at a given wavelength a ratio of the second fluorescence emission spectrum and the first fluorescence emission spectrum at least for the liquid polymerizable composition and for after curing of the cured polymer so that the extent of curing can be determined.

As used herein, and in the appended claims, unless the contrary is indicated, the following terms refer to:

cured polymer: a chemical reaction wherein conversion of monomers or prepolymers to polymers has achieved sufficient completion.

monomer: small molecules which may combine with one another to form long chains of molecules which can be polymers or prepolymers.

polymer: long chains of chemically interlinked monomers solvatochromic probe molecule: molecules added to the polymerizable composition which respond to a physical change in the polymerizing system such that the degree of cure of the polymer can be monitored effectively and whose emission spectra shift in proportion to the polarity of the local environment polymerizable composition: a composition in which monomers or prepolymers have not yet reacted sufficiently with one another to form the cured polymer.

The present invention provides a novel fluorescence monitoring method and apparatus utilizing a solvatochromic probe which exhibits a shift in fluorescence wavelength or intensity with increasing cure. The use of the solvatochromic probe avoids many of the problems and pitfalls associated with viscosity-sensitive fluorescence used by the prior art. First, the solvatochromic method is based upon the relative fluorescence intensity ratio of two interdependent peaks or points in the emission spectrum, thereby avoiding the problems (such as broadband background interference) associated with absolute fluorescence intensity measurements. In addition, unlike the viscosity-sensitive fluorescence probes, the solvatochromic probe does not lose sensitivity after the gel point (where the viscosity has diverged).

The use of solvatochromic probe molecules to study chemical and/or physical phenomena hinges on the sensitivity of the probe molecule to some changing property of its local environment. Two such changes are the polarity and structural rigidity of the local environment. In addition, for the probe molecule to be useful it must also have a large absorptivity and a moderately high fluorescence quantum yield, so that the information about its local environment can be measured efficiently. The fluorescent probe molecule is preferably used in trace amounts, such as between about $10^{-4}$ and $10^{-3}$ weight percent of the polymerizable composition. The molecule is also preferably nonreactive in the polymer and does not adversely affect the properties of the polymerizable composition.

The solvatochromic probe molecules are, for instance: oxazones (such as phenoxazone), pyrene, and oxazines (see Blanchard, G. J., Chemical Physics 365–375 (1989); and Karpovich and Blanchard, J. Phys. Chem. 99:3951–3958 (1995)).

The polymers are preferably poly(vinyl) polymers of various well known types including methacrylates, styrenes, unsaturated polyester resins, and vinyl ester resins, (such as the DERAKANE resins). The initiators are standard free radical initiators such as peroxy and azo compounds, ketones, redox-systems and the like.

Monitoring changes in a polymerization reaction in real time and in the presence of potential background interferences places limits on the ways in which the measurement can be accomplished. Measuring an absolute quantity is practical only if the background is known, and preferably constant in time. For this reason, absolute emission intensity is not as suitable for long-term on-line or process-control measurements. The solvatochromic probe molecule fluorescence lifetime is an absolute quantity which can be resolved from the background since measurement of this quantity depends on time registration introduced by the instrumentation (background interference will not be synchronous). Such a measurement is, however, technologically involved (Holtom, G. R., ASTM Proceedings 1204-01 1 (1990)) and not likely to be useful for practical chemical processing situations. A more practical approach for probe molecule-based monitoring is to measure the position or shape of the probe emission band as a function of environment. A particularly simple way to do this is to monitor two different emission wavelengths, as shown in FIG. 1, and take the ratio of the intensities at the two wavelengths (Tan, W., et al., Science 258 778 (1992)) as exemplified on FIG. 1 and in FIG. 3. Measuring the ratio rather than absolute intensities eliminates many uncertainties associated with macroscopic inhomogeneities and broadband background interferences such as scattered white light.

EXAMPLE 1

An epoxy vinyl ester resin solution containing styrene (33% by weight) was prepared by mixing DERAKANE 411-C50 supplied by Dow Chemical, Midland, Mich. The resin was cured with 0.75 wt % 2,2'-azobisisobutyronitrile (AIBN) as an initiator and contained $10^{-4}$ wt % phenoxazone 660 (9-diethylamino-5H-benzo(a)phenoxazin-5-one), of the formula:

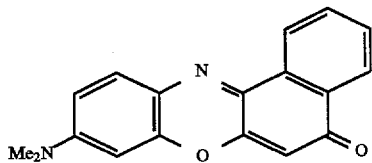

where Me is methyl. The sample was placed in a glass cuvette and cured in an Aminco-Bowman Series 2 (Urbana, Ill.) Luminescence spectrometer at 70° C. The sample emission spectrum was recorded every five minutes for 60 minutes using an excitation frequency of 540 nm.

Figure 2:
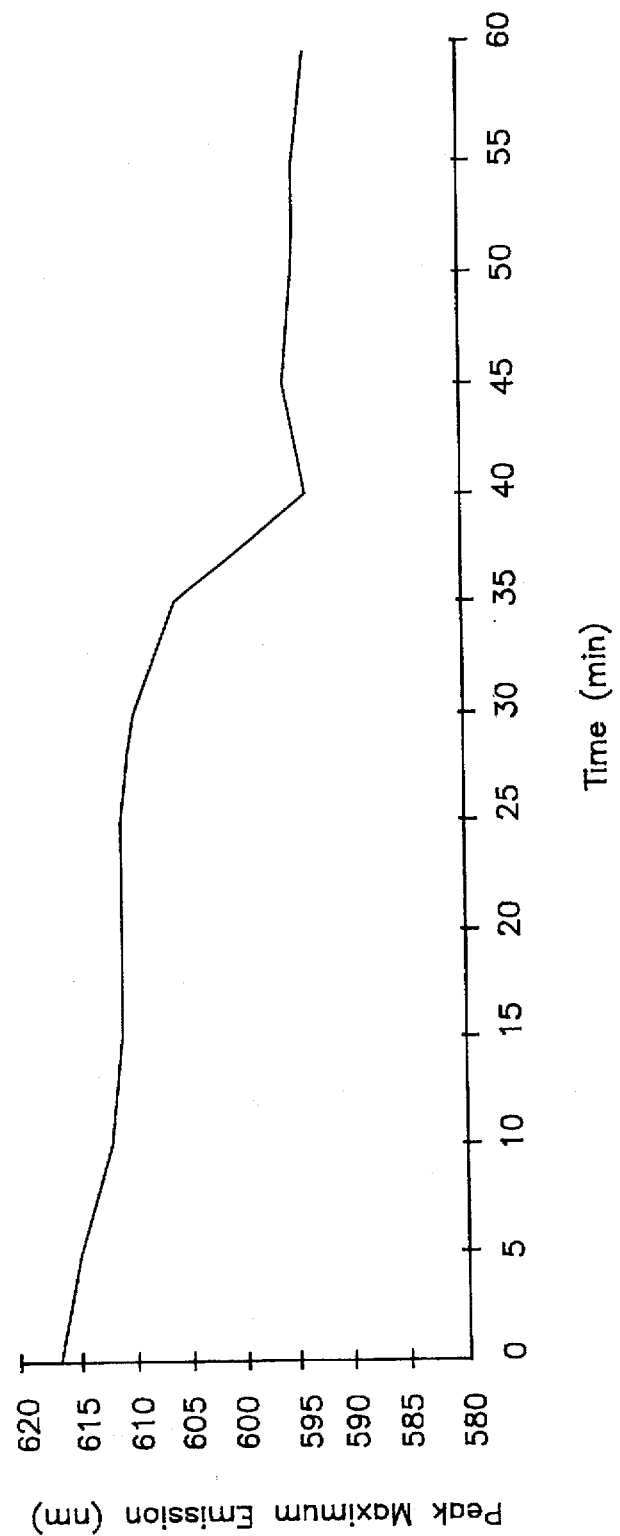
FIG. 2 is a graph of peak emission wavelength versus time determined using a fluorimeter with the DERAKANE composition as in Example 1 and FIG. 1 at 70° C. and at 540 nm excitation.
Figure 3:
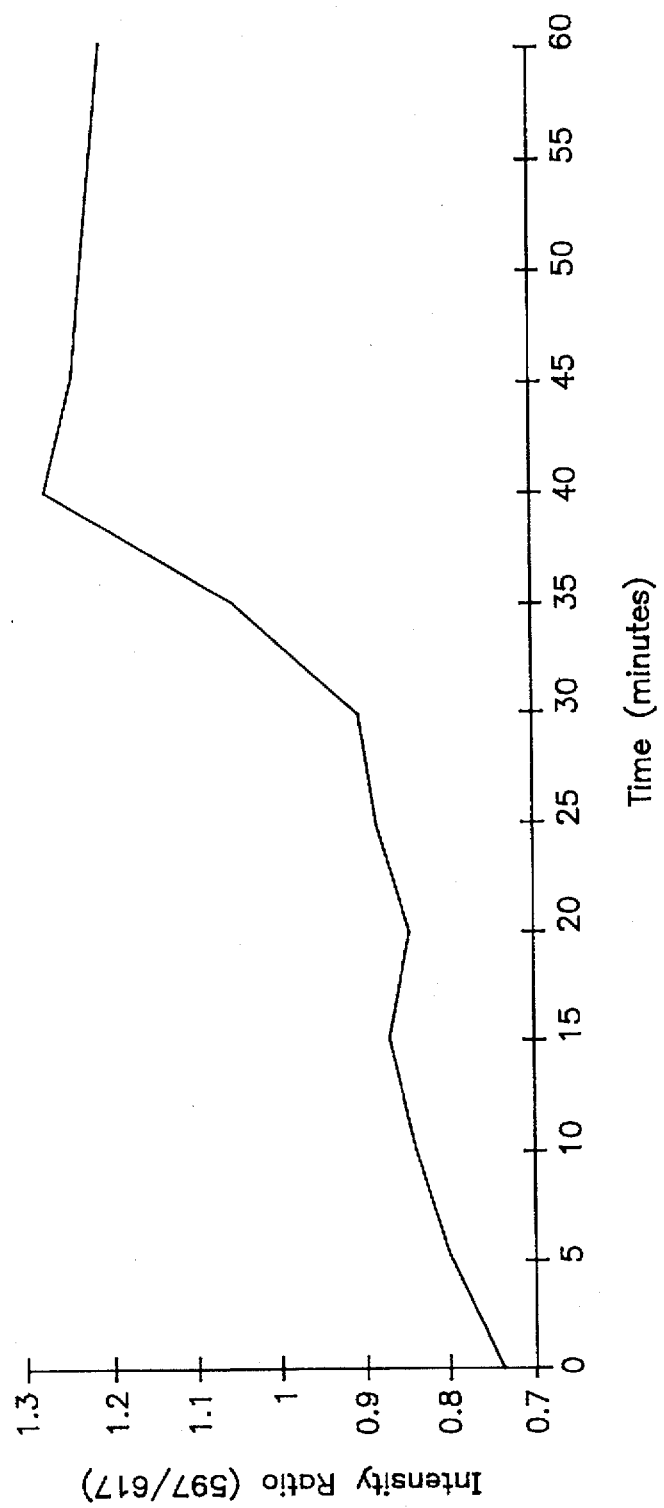
FIG. 3 is a graph showing the intensity ratio at two different wavelengths (597 and 617 nm) as a function of time at 70° C. with excitation at 540 nm.

The fluorescence emission maximum or peak of phenoxazone 660 blue-shifts from 617 nm to 597 nm during cure, as shown in FIGS. 1 and 2. By calculating $I_{597}/I_{617}$ for instance, it is easy to distinguish between an uncured system with $I_{597}/I_{617}=0.7$ and a cured system with $I_{597}/I_{617}=1.2$. FIG. 3 shows the intensity ratio as a function of time at 70° C. with excitation at 540 nm.

The solvatochromic effect of the phenoxazone appears to occur because the (excited state) population of the non-bonding orbital associated primarily with the ring-bound nitrogen depends on the extent to which it is solvated. Interaction of this lone pair with the local environment determines its energy with respect to the excited state of the molecule and thus its coupling to the chromophore. This tunable degree of "delocalization" is highly selective for interactions with the ring-bound nitrogen.

In order to determine the origin(s) of the observed spectral shift, the emission spectra of phenoxazone 660 were recorded in a series of solvents spanning a range of polarity. For each solvent (Table 1), the wavelength of the phenoxazone 660 emission maximum is listed along with the values of $E_T(30)$ (one measure of solvent polarity), $\epsilon_0$ (dielectric constant), $\pi^*$ (a second measure of solvent polarity), and $\mu$ (dipole moment). The data in Table 1 show that the best correlation is between emission maximum and solvent $\pi^*$ value. These studies suggest that the shift in the phenoxazone 660 emission arises from alteration of the local polarity-polarizability during cure.

TABLE 1

Comparison of solvent polarity and phenoxazone 660 emission maximum

| Solvent | emission maximum | $E_T(30)$ | $\epsilon_0$ | $\mu$ (Debye) | $\pi^*$ |
|---|---|---|---|---|---|
| THF | 595 nm | 37.4 | 7.6 | 1.63 | 0.58 |
| Acetone | 612 nm | 42.2 | 20.7 | 2.88 | 0.68 |
| Acetomtrile | 617 nm | 46.0 | 37.5 | 3.92 | 0.86 |
| DMF | 623 nm | 43.8 | 36.7 | 3.82 | 0.88 |
| DMSO | 633 nm | 45.0 | 4.7 | 3.96 | 1.00 |

EXAMPLE 2

An acrylic monomer solution was prepared by mixing methyl methacrylate (MMA) monomer of the formula:

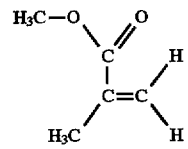

with 1 wt % 2,2'-azobis (2,4-dimethyl-4-methoxy valeronitrile) initiator of the formula:

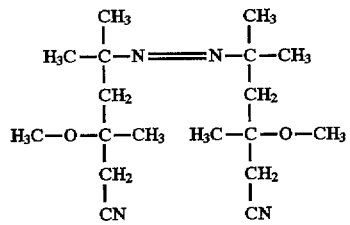

and $10^{-3}$ wt % pyrene as a probe molecule of the formula:

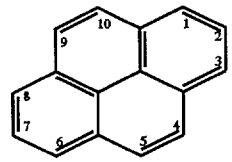

The sample was placed in a glass bulb connected to a glass cuvette and subjected to three freeze-pump-thaw cycles to remove the oxygen from the monomer solution. The sample was then transferred to the glass cuvette and cured in an Aminco-Bowman Series 2 Luminescence spectrometer at 40° C. The sample emission spectrum was recorded every five minutes for 150 minutes using an excitation frequency of 330 nm.

Calculating a Fixed Time Ratio

The polymer has reached the completion of cure when the following ratio of emission intensities increases dramatically with respect to time and then levels out at some constant value (FIG. 7):

$$\frac{I_1}{I_2} = \frac{\text{Intensity of specific emission wavelength at } t > 0}{\text{Intensity of specific emission wavelength at } t = 0}$$

Tables 2 and 2A show the results at 378 nm and 389 nm.

TABLE 2

Time Averages for 378 nm Wavelength

| t, min | Abs Intensity | Fixed Time Ave |
|---|---|---|
| 0 | 16.8831 | 1 |
| 5 | 13.3247 | 0.789233 |
| 10 | 12.1369 | 0.718879 |
| 15 | 11.4194 | 0.676381 |
| 20 | 12.1429 | 0.719234 |
| 25 | 12.7261 | 0.753777 |
| 30 | 11.685 | 0.692112 |
| 35 | 12.192 | 0.722142 |
| 40 | 12.031 | 0.712606 |
| 45 | 13.2989 | 0.787705 |
| 50 | 14.1009 | 0.835208 |
| 55 | 14.9581 | 0.885981 |
| 60 | 15.1102 | 0.89499 |
| 65 | 15.3453 | 0.908915 |
| 70 | 15.9458 | 0.944483 |
| 75 | 17.5711 | 1.040751 |
| 80 | 108.456 | 6.423939 |
| 85 | 248.131 | 14.697 |
| 90 | 291.197 | 17.24784 |
| 95 | 297.867 | 17.64291 |
| 100 | 293.786 | 17.40119 |
| 105 | 301.353 | 17.84939 |
| 110 | 303.764 | 17.99219 |
| 115 | 300.324 | 17.78844 |
| 120 | 301.098 | 17.83428 |
| 125 | 300.324 | 17.78844 |
| 130 | 306.124 | 18.13198 |
| 135 | 305.44 | 18.09146 |
| 140 | 307.393 | 18.20714 |
| 145 | 303.948 | 18.00309 |
| 150 | 303.754 | 17.9916 |

TABLE 2A

Time Averages for 389 nm Wavelength

| t, min | Abs Intensity | Fixed Time Ave |
|---|---|---|
| 0 | 14.9837 | 1 |
| 5 | 15.5094 | 1.035085 |
| 10 | 13.5363 | 0.903402 |
| 15 | 12.2502 | 0.817568 |
| 20 | 12.7199 | 0.848856 |
| 25 | 13.6364 | 0.910082 |
| 30 | 13.3506 | 0.891008 |
| 35 | 13.5626 | 0.905157 |
| 40 | 13.4977 | 0.900826 |
| 45 | 13.5626 | 0.905157 |
| 50 | 14.1375 | 0.943525 |
| 55 | 15.4739 | 1.032716 |
| 60 | 15.623 | 1.042666 |
| 65 | 16.23 | 1.083177 |
| 70 | 17.3377 | 1.157104 |
| 75 | 19.1586 | 1.278629 |
| 80 | 130.479 | 8.708063 |
| 85 | 234.903 | 15.67724 |
| 90 | 267.974 | 17.88437 |
| 95 | 277.399 | 18.51338 |
| 100 | 276.261 | 18.43744 |
| 105 | 277.276 | 18.50518 |
| 110 | 288.285 | 19.23991 |
| 115 | 281.854 | 18.81071 |
| 120 | 277.132 | 18.49557 |
| 125 | 277.613 | 18.52767 |
| 130 | 276.535 | 18.45572 |
| 135 | 290.821 | 19.40916 |

TABLE 2A-continued

Time Averages for 389 nm Wavelength

| t, min | Abs Intensity | Fixed Time Ave |
|---|---|---|
| 140 | 281.113 | 18.76125 |
| 145 | 281.623 | 18.79529 |
| 150 | 281.871 | 18.81184 |

Calculating a Rolling Time Ratio

The polymer has reached the completion of cure when the following ratio of emission intensities peaks dramatically with respect to time and then levels out to the original constant value (FIG. 8):

$$\frac{I_1}{I_2} = \frac{\text{Intensity of specific emission wavelength at } t = n}{\text{Intensity of specific emission wavelength at } t = n - 1}$$

Tables 3 and 3A show the rolling time ratio results at 378 nm and 389 nm:

TABLE 3

Time Averages for 378 nm Wavelength

| t, min | Abs Intensity | Rolling Time Ave |
|---|---|---|
| 0 | 16.8831 | — |
| 5 | 13.3247 | 0.789233 |
| 10 | 12.1369 | 0.910857 |
| 15 | 11.4194 | 0.940883 |
| 20 | 12.1429 | 1.063357 |
| 25 | 12.7261 | 1.048028 |
| 30 | 11.685 | 0.918192 |
| 35 | 12.192 | 1.043389 |
| 40 | 12.031 | 0.986795 |
| 45 | 13.2989 | 1.105386 |
| 50 | 14.1009 | 1.060306 |
| 55 | 14.9581 | 1.06079 |
| 60 | 15.1102 | 1.010168 |
| 65 | 15.3453 | 1.015559 |
| 70 | 15.9458 | 1.039133 |
| 75 | 17.5711 | 1.101927 |
| 80 | 108.456 | 6.172408 |
| 85 | 248.131 | 2.287849 |
| 90 | 291.197 | 1.173562 |
| 95 | 297.867 | 1.022905 |
| 100 | 293.786 | 0.986299 |
| 105 | 301.353 | 1.025757 |
| 110 | 303.764 | 1.008001 |
| 115 | 300.324 | 0.988675 |
| 120 | 301.098 | 1.002577 |
| 125 | 300.324 | 0.997429 |
| 130 | 306.124 | 1.019312 |
| 135 | 305.44 | 0.997766 |
| 140 | 307.393 | 1.006394 |
| 145 | 303.948 | 0.988793 |
| 150 | 303.754 | 0.999362 |

TABLE 3A

Time Averages for 389 nm Wavelength

| t, min | Abs intensity | Rolling Time Ave |
|---|---|---|
| 0 | 14.9837 | — |
| 5 | 15.5094 | 1.035085 |
| 10 | 13.5363 | 0.87278 |
| 15 | 12.2502 | 0.904989 |
| 20 | 12.7199 | 1.038269 |
| 25 | 13.6364 | 1.072128 |

TABLE 3A-continued

Time Averages for 389 nm Wavelength

| t, min | Abs intensity | Rolling Time Ave |
|---|---|---|
| 30 | 13.3506 | 0.979041 |
| 35 | 13.5626 | 1.015879 |
| 40 | 13.4977 | 0.995215 |
| 45 | 13.5626 | 1.004808 |
| 50 | 14.1375 | 1.042389 |
| 55 | 15.4739 | 1.094529 |
| 60 | 15.623 | 1.009636 |
| 65 | 16.23 | 1.038853 |
| 70 | 17.3377 | 1.06825 |
| 75 | 19.1586 | 1.105025 |
| 80 | 130.479 | 6.810466 |
| 85 | 234.903 | 1.800313 |
| 90 | 267.974 | 1.140786 |
| 95 | 277.399 | 1.035171 |
| 100 | 276.261 | 0.995898 |
| 105 | 277.276 | 1.003674 |
| 110 | 288.285 | 1.039704 |
| 115 | 281.854 | 0.977692 |
| 120 | 277.132 | 0.983247 |
| 125 | 277.613 | 1.001736 |
| 130 | 276.535 | 0.996117 |
| 135 | 290.821 | 1.051661 |
| 140 | 281.113 | 0.966619 |
| 145 | 281.623 | 1.001814 |
| 150 | 281.871 | 1.000881 |

Figure 4:
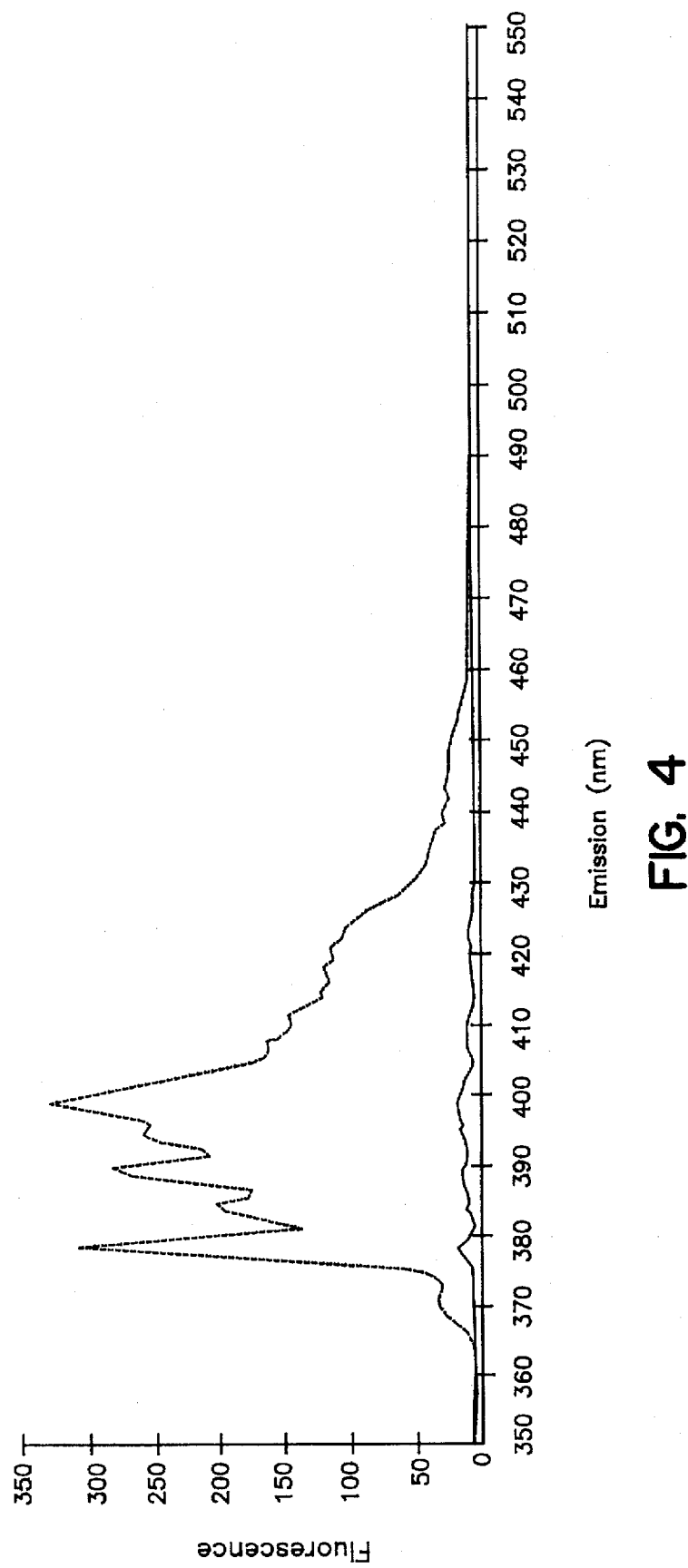
FIG. 4 is a graph of fluorescence intensity versus light emission at the listed wavelengths for methyl methacrylate cured with 1 weight percent 2,2'-azobis(2,4-dimethyl-4-methoxy valeronitrile) (V-70) as an initiator and $10^{-3}$ weight percent pyrene as a probe molecule at 40° C. and at 330 nm excitation as in Example 2. The solid line is for zero minutes and the dotted line is after 150 minutes.
Figure 5:
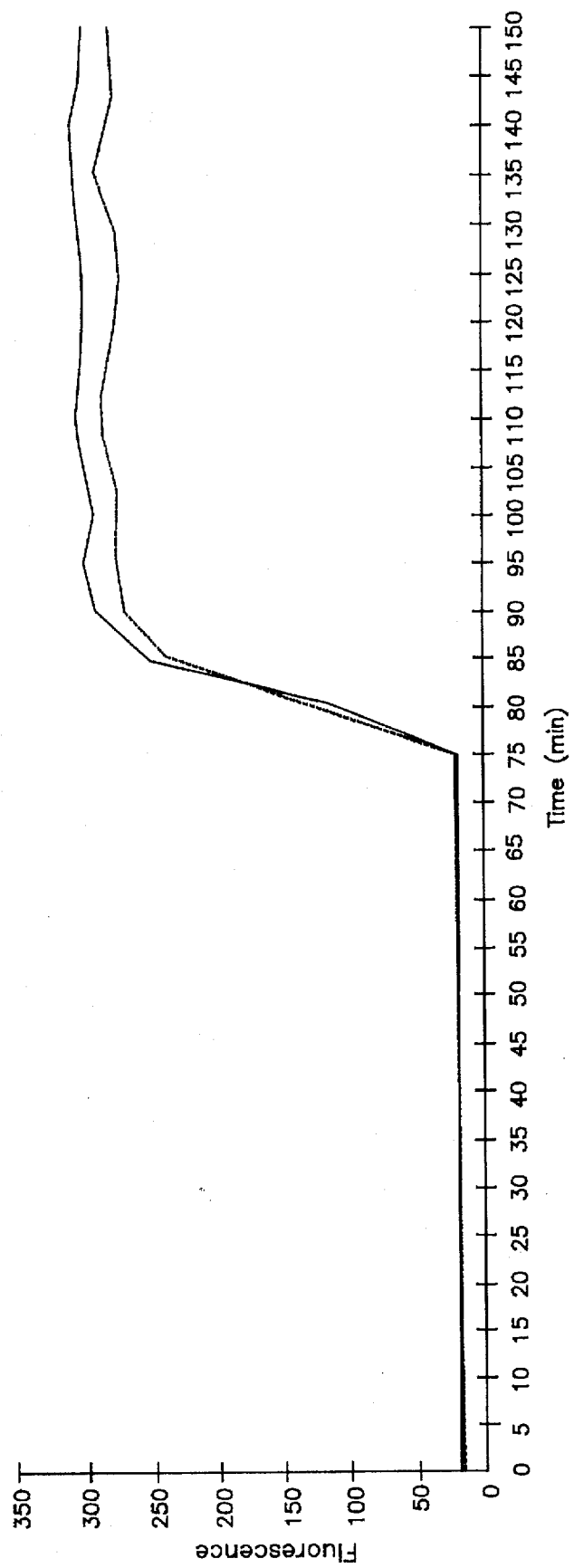
FIG. 5 is a graph showing intensity of fluorescence versus time at 378 nm (solid line) and at 389 nm (dotted line) for the polymerizable composition of Example 2.
Figure 6:
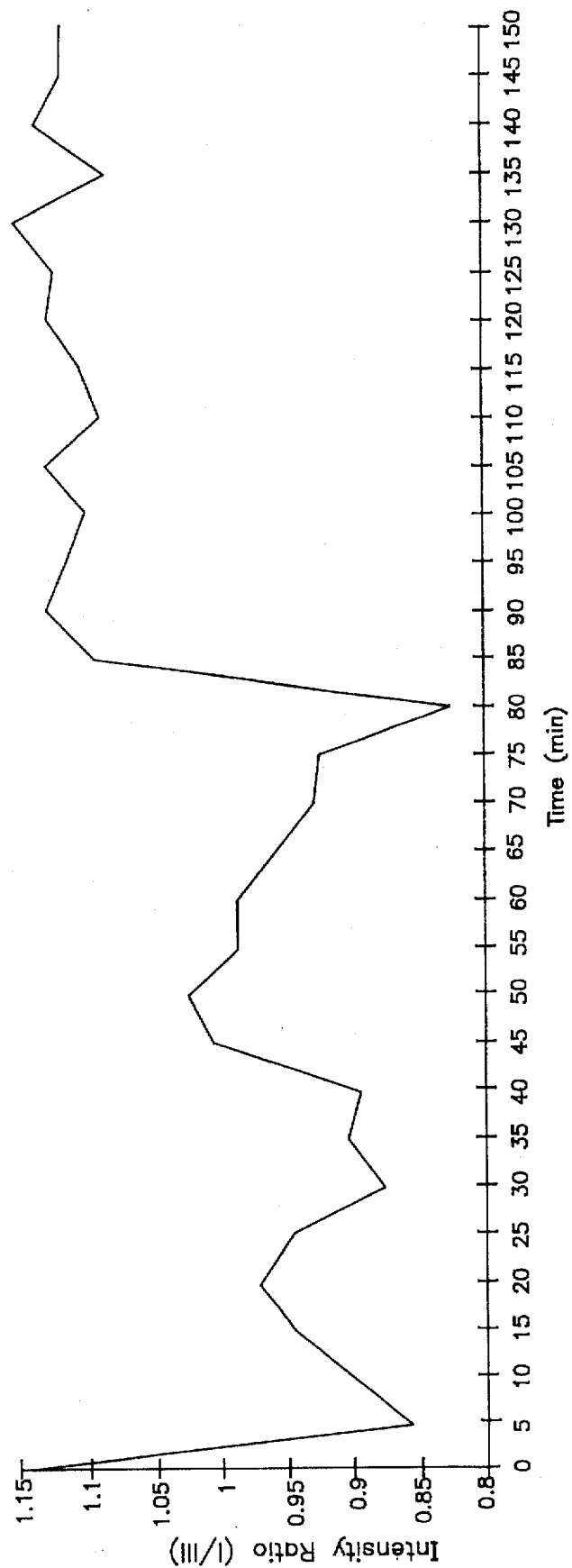
FIG. 6 is a graph showing the intensity ratio (I/III) of the polymerizable composition as shown in FIG. 4 at 378 nm (I) and at 389 nm (III).
Figure 7:
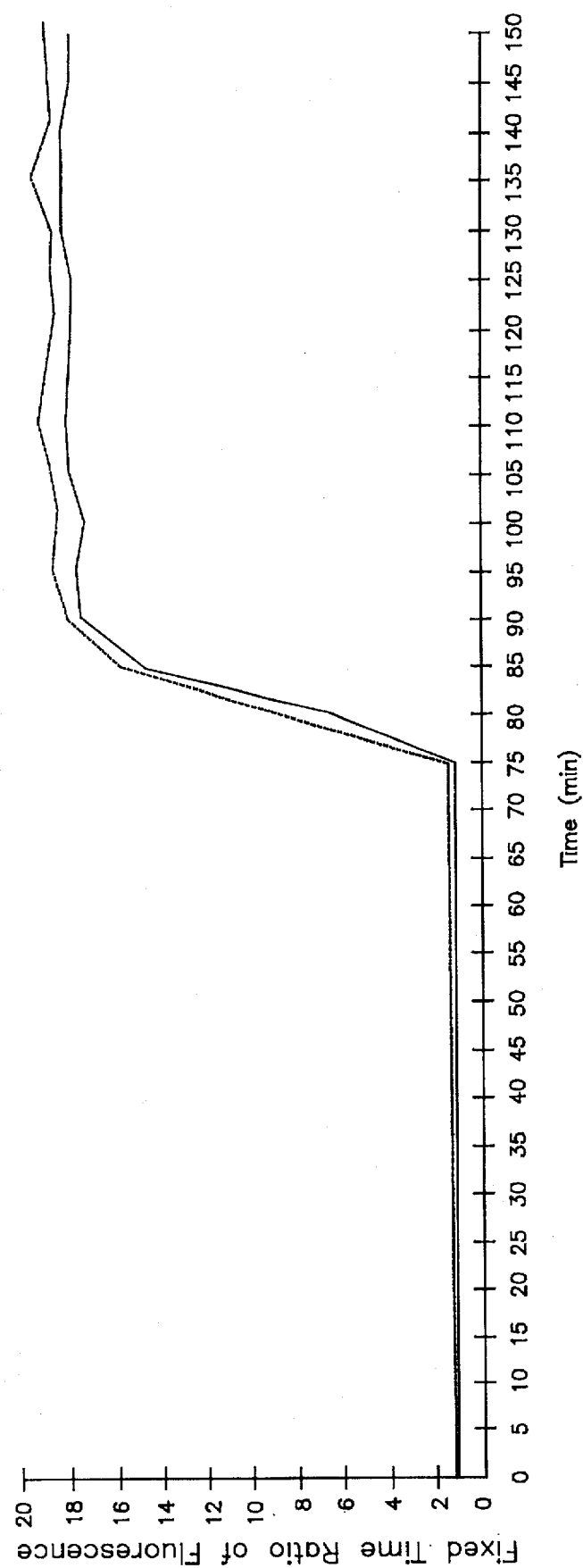
FIG. 7 is a graph showing the fixed time ratios of fluorescence at 378 nm (solid line) and at 389 nm (dotted line) from time zero to the end.
Figure 8:
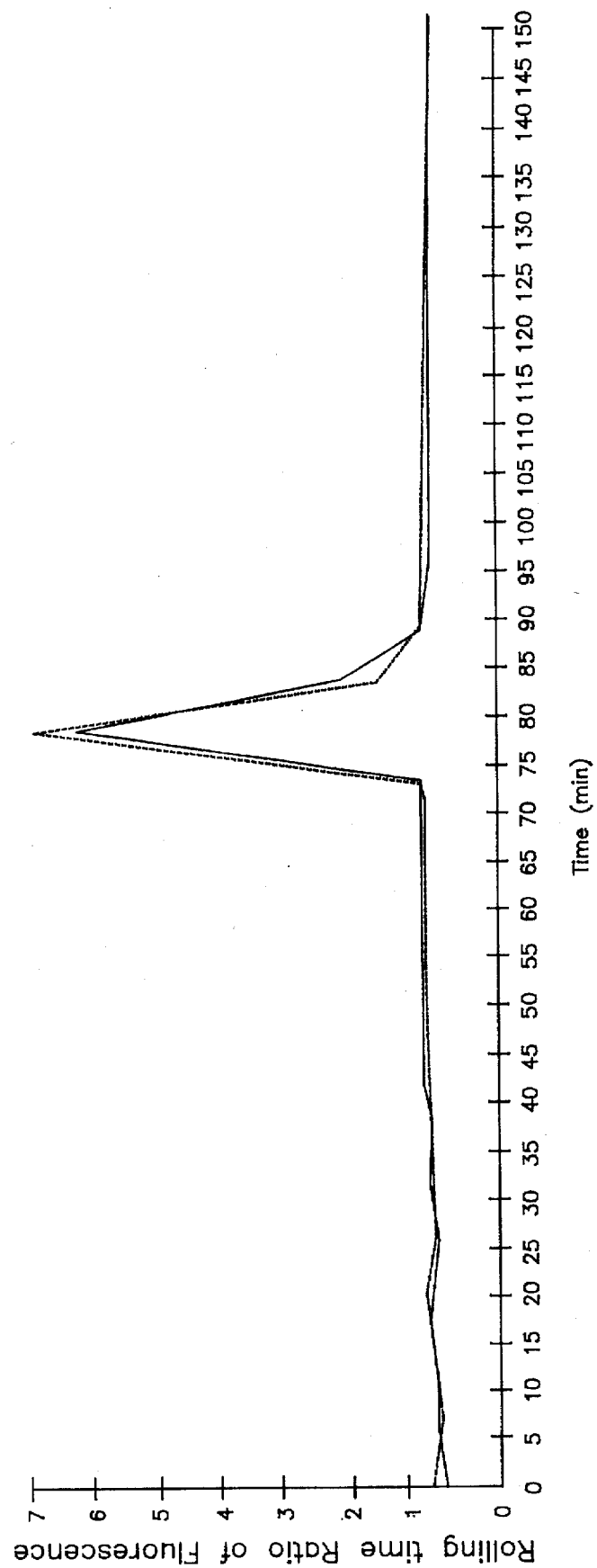
FIG. 8 is a graph showing a rolling time ratio of fluorescence for the composition of Example 2, wherein the interval is five (5) minutes. The solid line is the ratio at 378 nm at t=n to 378 nm at t=n−1. The dotted line is the ratio at 389 nm at t=n to 389 at t=n−1. As can be seen, a distinct peak is produced at cure or completion.

The fluorescence emission intensities of pyrene increased one order of magnitude during cure, as shown in FIGS. 4 and 5. A ratio of the two (bands) in the emission spectrum, namely those at 378 nm and 389 nm, is shown to rise to a second plateau when the polymer sample cures as shown in FIG. 6. However, the most drastic proof of cure is found in taking either a fixed time ratio of fluorescence (the reference fluorescence being at time zero), as shown in FIG. 7, or a rolling time ratio of fluorescence (the reference fluorescence being five minutes previous to the point of interest), as shown in FIG. 8. In both graphs, it is relatively easy to distinguish between an uncured system and a cured system by noting the steep change in the ratio of fluorescence vs. time slopes.

EXAMPLE 3

In order to design and operate a practical monitoring apparatus, special emphasis is placed on the simplicity of the measurement and the robust nature of the apparatus.

Figure 9:
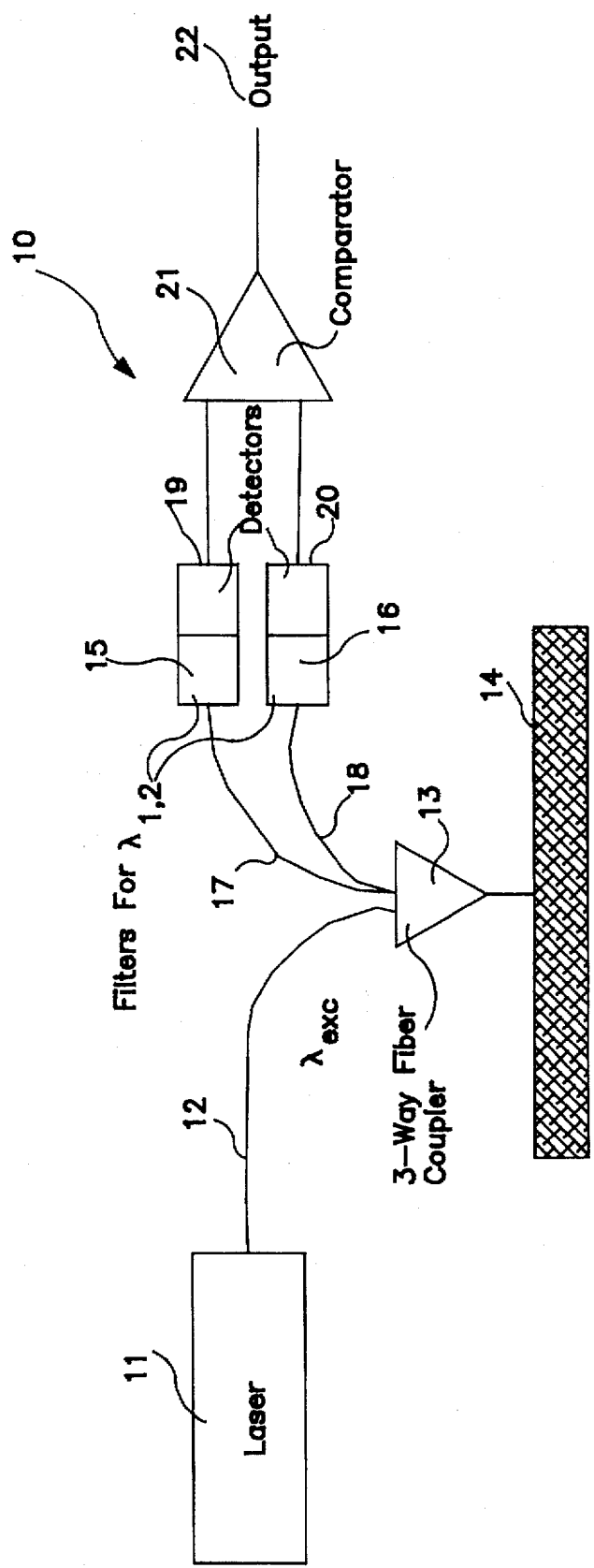
FIG. 9 is a drawing showing an apparatus for providing the $\lambda_{exc}$ for detecting the intensity I at $\lambda_1$ and $\mu_2$ and for comparing the intensity I at $\lambda_1$ and $\lambda_2$.

As shown in FIG. 9, an apparatus 10 was provided with a laser 11 connected at a proximal end of a light cable 12. A distal end of the cable 12 was connected to a three-way fiber coupler 13 such that the light ($\lambda_{exc}$) impinges on a surface of the curing polymer 14. The fluorescence generated was directed to filters 15 and 16 by cables 17 and 18. The fluorescence intensity was detected by detectors 19 and 20 and the electrical output of each was directed to a comparator 21 which determines when a shift in the wavelength of fluorescence was sufficient to produce a cured polymer. FIG. 1 shows a ratio of $I\mu_2/I\lambda 1=4$ at 580 nm and 628 nm. At 580 nm and 628 nm, the ratio is about 0.8 for the cured polymer. The larger the change before cure in the ratio, the easier the determination of the degree of curing. The output 22 of the comparator 21 was used to determine whether or not a cure has been achieved.

A laser (such as laser 11) is the light source of choice for such measurements because of its inherent spectroscopic selectivity and the favorable properties of the output beam, thereby requiring a minimum of conditioning optics. Routing the excitation light to the process of interest did not involve optical components, such as mirrors or lenses, both for reliability and safety reasons. Fiber optic cables were preferably used to route the excitation light to the analyte and then to collect the emission from the surface and send it to the detection system such as comparator 21. Optical fibers are available which transmit UV and visible light with comparatively low optical loss, and thus are ideally suited to this type of apparatus. Other light sources besides lasers can be used.

For a particular probe molecule, inexpensive optical detection components optimized for predetermined wavelengths were chosen and incorporated into the fiber optic-based remote sensing system. Optical notch filters (filters 15 and 16) are used to separate $\lambda_1$ and $\lambda_2$ from $\lambda_{exc}$ and sensitive solid state detectors were used for each wavelength $\lambda_1$ and $\lambda_2$. Measurement of the ratio of the output from the two detectors over time was accomplished using a comparator 21.

The output of the apparatus was proportional to the ratio of intensity measured at $\lambda_1$ and $\lambda_2$. Calibration of the system was accomplished using two standards for the process: one where no curing has been allowed to occur and the other where the polymer is completely cured. Construction of the apparatus was straightforward and was accomplished using inexpensive commercial components.

For phenoxazone 660, as in Example 1, inexpensive optical detection components optimized for pre-determined wavelengths were chosen and incorporated into a fiber optic-based remote sensing system. Optical notch filters were used to separate 617 nm ($\lambda_1$) and 597 nm ($\lambda_2$) from 540 nm ($\lambda_{exc}$), and sensitive solid state detectors were used for each monitoring wavelength. The output of such a system was proportional to the difference in intensity measured at 617 nm and 597 nm. In the DERAKANE system, phenoxazone 660 exhibits a shift in the wavelength of maximum fluorescence intensity from 617 nm in the uncured system to 597 nm in the fully cured system as shown in FIG. 1. This shift was found to correlate with the local polarity-polarizability as characterized by $\pi^*$. The intensity ratio of these two peaks over time as in FIG. 3, provides a measure of the degree of cure which is insensitive to background interferences and does not lose sensitivity after the gel point.

It is intended that the foregoing description be only illustrative and that the present invention be limited only by the hereinafter appended claims.

We claim:

1. An apparatus for determining an extent of curing of a cured polymer which comprises:

(a) a detection means which measures a shift in fluorescence emission spectrum during polymerization of a liquid polymerizable composition to the cured polymer from a solvatochromic probe molecule, which is a polycyclic aromatic compound in an amount up to about $10^{-3}$ weight percent of the polymerizable composition, wherein the probe molecule has a first fluorescence emission spectrum in the liquid polymerizable composition and a shifted second fluorescence emission spectrum in the cured polymer, wherein the detection means includes a probe means mounted adjacent to the polymer for detecting the fluorescence;

(b) a light source which can be directed at the polymerizable composition so that the fluorescence emission spectrum produced by the probe molecule is detected by the probe means;

(c) a support for the fluid polymer during the curing to the cured polymer; and (d) calculating means for calculating at a given wavelength a ratio of the second fluorescence emission spectrum and the first fluorescence emission spectrum at least for the liquid polymerizable composition and during the polymerization to the cured polymer so that the extent of curing can be determined, and wherein the shift in the fluorescence is detected beyond a gel point of the polymer.

2. The apparatus of claim 1 wherein the detection means and calculating means are operable at pre-selected intervals of time during the curing.

3. The apparatus of claim 1 wherein the light source is a laser.

4. The apparatus of claim 1 wherein the probe means is connected to an optical cable so that the light from the light source is directed at the reaction mixture.

* * * * *